United States Patent [19]

Womack

[11] 4,425,124
[45] Jan. 10, 1984

[54] CATHETER ASSEMBLY

[76] Inventor: Charles E. Womack, 594 Cypress Dr., Florence, Ala. 35630

[21] Appl. No.: 251,860

[22] Filed: Apr. 6, 1981

[51] Int. Cl.³ .............................................. A61F 5/44
[52] U.S. Cl. .................................. 604/283; 604/128; 604/326; 604/94
[58] Field of Search ................... 128/348, 349 R, 247, 128/275, 295, 760, 767, 768; 604/94, 128, 129, 246, 280–283, 322–326

[56] References Cited

U.S. PATENT DOCUMENTS

| 3,943,929 | 3/1976 | Patel | 128/275 |
| 3,990,447 | 11/1976 | Vega | 128/349 R |
| 4,159,022 | 6/1979 | Pevsner | 128/348 X |
| 4,265,243 | 5/1981 | Taylor | 128/275 |

FOREIGN PATENT DOCUMENTS 375579  6/1932  United Kingdom ............ 128/349 R

Primary Examiner—Dalton L. Truluck
Attorney, Agent, or Firm—C. A. Phillips

[57] ABSTRACT

A catheter assembly wherein Foley and ureteral catheters and a drainage bag are all coupled together by a coupling chamber. The coupling chamber has an entrance at one end for the Foley catheter and a drainage exit at an opposite end. Two secondary chambers extend outward from and connect to the mid region of the central chamber, and each is connectable to a ureteral catheter.

4 Claims, 6 Drawing Figures

U.S. Patent   Jan. 10, 1984   Sheet 2 of 2   4,425,124

CATHETER ASSEMBLY

TECHNICAL FIELD

This invention relates generally to catheters for the urinary tract, and particularly to a catheter assembly for the handling of drainage from the bladder and kidneys.

BACKGROUND ART

It is a common medical practice to simultaneously effect drainage from both the bladder and one or more kidneys of a patient. Such procedure is typically accomplished by the employment of a Foley catheter to the bladder, which has a balloon which holds it in place, and one or two ureteral catheters are mechanically secured in place by a support from the Foley catheter.

The applicant, a urologist, has observed that there is simply no available system of both practically and economically managing urine flow when the two types of catheterization are employed.

As matters stand, the physician has two known choices. One is to simply couple the drainage outputs of the Foley and ureteral catheters to separate drainage bags. This, of course, requires two or more complete drainage systems, including two or more drainage bags. This is both costly and cumbersome, but this approach is widely used because of the lack of a better system available. The second choice, the one least generally employed, requires that a hole be punched in the Foley catheter for each ureteral catheter tube, each tube being inserted through the hole in the Foley catheter into the drainage tube leading to the urinary drainage bag. Neither the hole punching nor the insertion step is easy, as the Foley tubing is quite soft and flexible, and several tries may be necessary. This is both frustrating and time-consuming. Equally, or of a greater problem, is the fact that there is often leakage of urine from such improvised connections and contamination of the system by bacteria. Still another problem is that by the insertion into the Foley catheter, a ureteral catheter may kink or otherwise become obstructed and flow through it becomes blocked.

Considering the difficulties with the "cut and insert" method, it is surprising that it has been a method used for at least the past 10 years; and to the applicant's knowledge, no acceptable substitute has been found. Accordingly, it is the object of this invention to provide one.

DISCLOSURE OF THE INVENTION

In accordance with this invention, a combining chamber is employed which couples the outputs of the bladder and ureteral catheters to a single drainage bag. This chamber is formed with a generally straight, elongated, central passageway with one end, an upper end, connected to a tubular output of the bladder catheter, and an opposite, or lower, end connected through a tube to the drainage bag. A pair of tubular members extend outward from the central passageway, and a ureteral catheter tube is connectable to an end of one of these by a collar and ferrule combination. Thus, by the system described, both bladder and kidney drainage is conveniently and effectively provided into a single drainage bag.

BRIEF DESCRIPTION OF THE DRAWINGS

FIG. 6 is an end view of a cap member employed to close off one of the entrances of the fluid combining chamber.

DETAILED DESCRIPTION OF THE DRAWING

Figure 2:
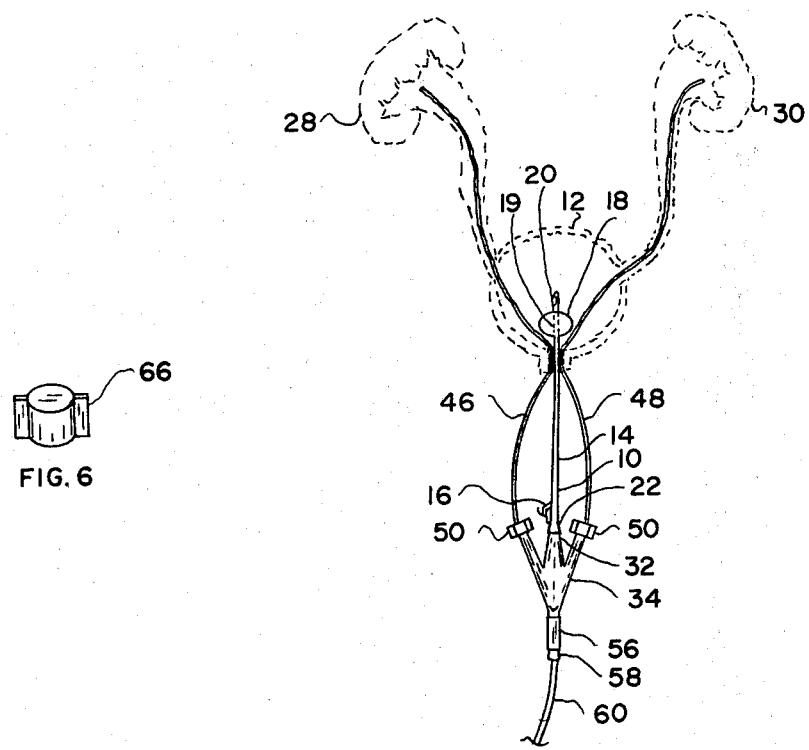
FIG. 2 is a side elevational view of a typical drainage bag employed by this system.
Figure 1:
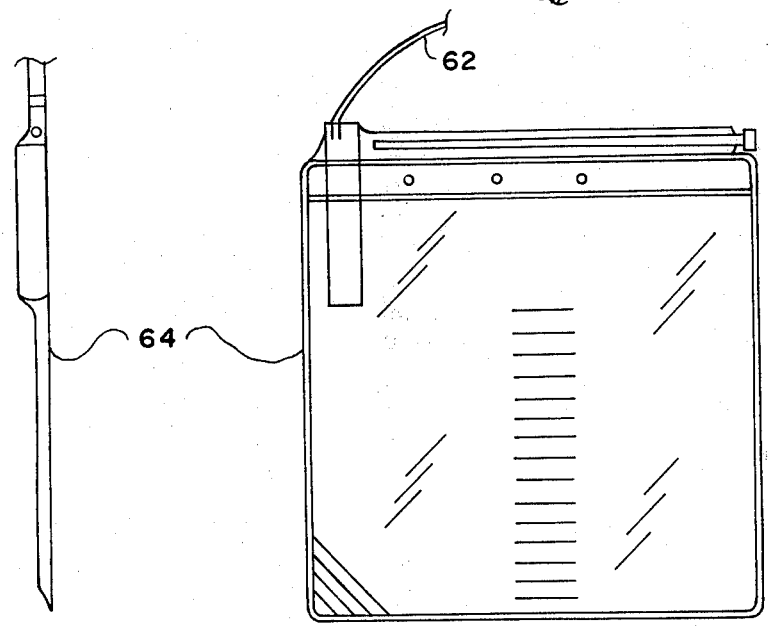
FIG. 1 is a front elevational view of the system of this invention.
Figure 4:
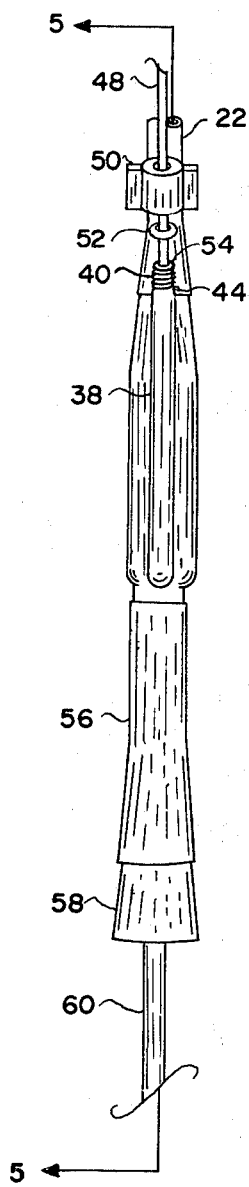
FIG. 4 is a side view of the structure shown in FIG. 3.
Figure 3:
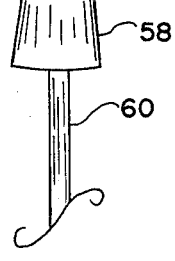
FIG. 3 is an enlarged frontal view of a central fluid combining chamber employed in the system of this invention.

Referring to the drawings, FIG. 1 shows a complete system arrangement of the invention. As shown, a standard Foley catheter 10 is illustrated in its functional position with respect to the bladder 12 of a patient. In the example shown, a tubular housing 14 contains an internal tube connected between an end 16 and balloon 18, whereby balloon 18 is expanded to thereby hold the catheter in place (as shown). Additionally, there is a drainage tube 19 extending through housing 14 which has an entrance 20 and exit tubular member 22.

Figure 5:
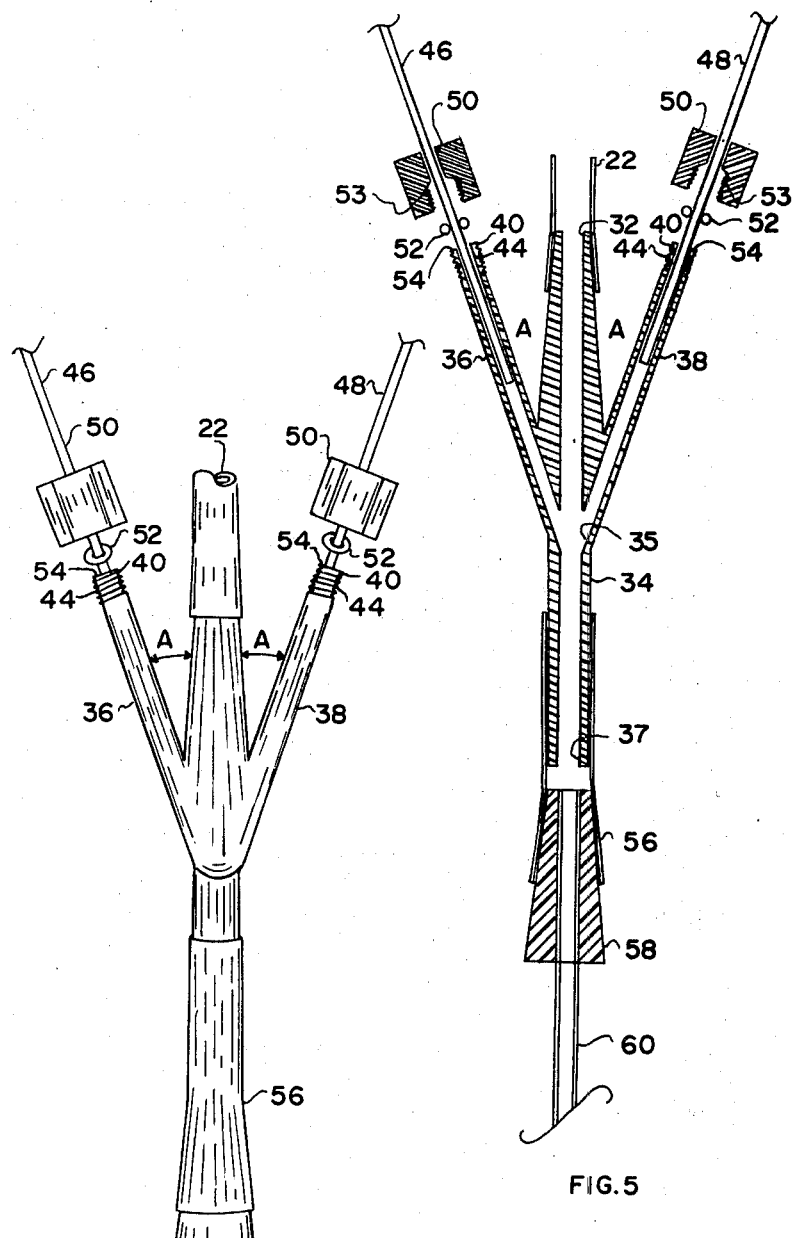
FIG. 5 is a sectional view taken along line 5—5 of FIG. 4.

Ureteral catheters or catheter tubes 46 and 48 are shown as having been inserted through bladder 12 to the kidneys 28 and 30 of a patient. End 22 of drainage tube 19 of Foley catheter 10 is slipped over the entrance end 32 of combining chamber 34. Chamber 34 is typically constructed of a rigid or semi-rigid plastic material and has a generally straight central region 35 (FIG. 5) which extends from entrance end 32 to an opposite, drainage, end 37. Two additional entrances are provided to chamber 34 by secondary tubular extensions 36 and 38, which extend generally in the direction of entrance 32, but are displaced from the basic central axis of chamber 34 by angle A of approximately 20°, typically an angle less than 90°, to enable a convenient and effective direction of tubing connections to chamber 34. The significant thing is that all tubes enter combining chamber 34 along a generally vertical path to insure unimpeded flow of fluid and compactness of their arrangement. Ends 40 of tubular extensions 36 and 38 have coupling threads 44. A ureteral catheter tube (46 or 48) is typically smaller than drainage tube 22 of Foley catheter 10, and one of these is inserted into an end 40 of tubular extensions 36 and 38. Where inserted, it is secured in place with a collar 50 which has threads 53 which thread onto threads 44 and compresses a ferrule or "O" ring 52 against a tube (46 or 48) and the face 54 of an end 40 of a tubular extension 36 or 38. Collar 50 is tapered inside (as shown in FIG. 5) so that when it is screwed onto threads 44, ferrule 52 is compressed inwardly to effect a seal between one end of one of the tubular extensions and a catheter tube.

Drainage end 37 of chamber 34 is coupled via a flexible coupling member or sleeve 56 to end coupling member 58 attached to drainage tube 60, which in turn is connected to tubular fitting 62 on a standard drainage bag 64 (FIG. 1).

In order to install the illustrated system, with Foley catheter 10 and ureteral catheters 46 and 48 in place as shown, the end 22 of exit or drainage tube 19 of Foley catheter 10 is simply slipped over entrance end 32 of combining chamber 34. Then, a collar 50 is slipped over each ureteral catheter tube (46 and/or 48) with a ferrule 52 and the collar 50 screwed on threaded end 40 of a tubular extension (36 or 38) to complete the connections of the exits of the tubes from the patient. This is accomplished simply and expeditiously. The outlet connection from combining chamber 34 is likewise a very simple procedure in that the drainage bag assembly is coupled by simply interconnecting coupling member 56 over and between end 37 of chamber 34 and coupling end 58 of tubing 60 leading to drainage bag 64.

In instances where only one ureteral catheter is employed, a cap 66, shown in FIG. 6, is attached to the otherwise unused tubular extension. It has a closed end and thus closes off the unused entrance of combining chamber 34. It is threaded in a configuration as shown by collar 50.

From the foregoing, it is to be appreciated that the invention both eliminates the problems incident to coupling a ureteral catheter to a Foley catheter and does it in such a manner as to eliminate the need of a separate drainage bag.

I claim:

1. A bladder and kidney drainage system comprising:
a bladder catheter assembly comprising a flexible outer tube including within it a plurality of flexible lumens, one of said lumens having a retention balloon at one end, and at least one lumen comprising a drainage tube having an entrance end adjacent to said retention balloon and having an opposite, drainage, end;
at least one ureteral catheter comprising a smaller tube than said drainage tube of said bladder catheter assembly, and means for supporting said ureteral catheter on said bladder catheter assembly;
a separate and disconnectable combining chamber comprising:
a generally straight passageway having an entrance opening at one end removably connected to said drainage end of said drainage tube, a single drainage exit comprising a tubular region at an opposite end, and a central region there between,
a pair of tubular coupling members extending outward from sides of said central region, the direction of extension of each having a directional component in the direction of the location of said entrance opening, whereby, with the entrance opening of said central chamber in an upper position, flow through said tubular coupling member enters said central region by virtue of gravity,
a threaded coupling end region on the end of each said tubular coupling member, and
coupling means including a ferrule adapted to surround an end region of a said tube of said ureteral catheter, and a collar adapted to fit around said last-named tube and over said ferrule, and having a threaded interior region adapted to thread onto said threaded coupling end region of said tubular coupling member, and thereby clamp together said last-named tube and said combining chamber;
a drainage bag;
a single elongated drain tube having an entrance end and an exit end, and said exit end being connected to said drainage bag, and having an enlarged tapered said entrance end; and
a coupling sleeve slidably coupled over said enlarged tapered entrance end of said drain tube and over said tubular region of said combining chamber.

2. A catheter as set forth in claim 1 further comprising a closing cap adapted to thread onto and close an end of a said secondary coupling chamber.

3. A catheter as set forth in claim 2 wherein the direction of a said tubular coupling member lies at an angle with respect to a line between the central region and said entrance opening of less than 90°

4. A catheter as set forth in claim 3 wherein the region around said entrance end of said combining chamber is tapered, being of a smaller diameter dimension at said entrance opening.

* * * * *